US008010382B2

(12) United States Patent
Chua et al.

(10) Patent No.: US 8,010,382 B2
(45) Date of Patent: Aug. 30, 2011

(54) SYSTEMS AND METHODS FOR SELF-UPDATING INTELLIGENT PROCEDURE DURATION ESTIMATION FOR PATIENT SCHEDULING

(75) Inventors: Wilkenson Chua, Lake Zurich, IL (US); Venkata Mrudula Gullapalli, Mount Prospect, IL (US); Vipul Patel, Bartlett, IL (US); Mariusz Kociubinski, Des Plaines, IL (US)

(73) Assignee: General Electric Company, Schenectady, NY (US)

( * ) Notice: Subject to any disclaimer, the term of this patent is extended or adjusted under 35 U.S.C. 154(b) by 237 days.

(21) Appl. No.: 12/211,132

(22) Filed: Sep. 16, 2008

(65) Prior Publication Data

US 2010/0070327 A1 Mar. 18, 2010

(51) Int. Cl.
*G06Q 10/00* (2006.01)
*G06Q 50/00* (2006.01)
*A61B 5/00* (2006.01)
*G06F 19/00* (2011.01)

(52) U.S. Cl. .............................................. 705/2; 705/3
(58) Field of Classification Search .................... 705/2–3
See application file for complete search history.

(56) References Cited

U.S. PATENT DOCUMENTS

| 5,623,404 | A | * | 4/1997 | Collins et al. ...................... 705/9 |
| 5,634,100 | A | * | 5/1997 | Capps ................................ 705/9 |
| 7,478,486 | B2 | * | 1/2009 | Wunderlin et al. ............. 34/491 |
| 2006/0004606 | A1 | * | 1/2006 | Wendl et al. ....................... 705/2 |

* cited by examiner

*Primary Examiner* — Luke Gilligan
*Assistant Examiner* — Joy Chng
(74) *Attorney, Agent, or Firm* — Hanley, Flight & Zimmerman, LLC

(57) ABSTRACT

Certain embodiments provide systems and methods for self-updating procedure duration estimation for patient scheduling. A scheduling system for scheduling procedures in a clinical environment includes historical procedure data including stored duration values for a procedure. The scheduling system also includes a user interface providing scheduling and procedure duration information to a user for scheduling the procedure for a patient. The scheduling system further includes a scheduling engine estimating one or more duration values for the procedure for scheduling the procedure for a patient. The scheduling engine establishes a default duration value for a procedure and updating the default duration value based on the historical procedure duration data. The scheduling engine provides a plurality of procedure durations including the updated default duration value to the user for selection via the user interface. The scheduling engine schedules a procedure using a user selected value for procedure duration.

8 Claims, 4 Drawing Sheets

SYSTEMS AND METHODS FOR SELF-UPDATING INTELLIGENT PROCEDURE DURATION ESTIMATION FOR PATIENT SCHEDULING

BACKGROUND TO THE INVENTION

The present disclosure relates generally to patient procedure scheduling, and, more particularly, to self-updating procedure duration estimation for patient scheduling.

Healthcare delivery institutions are business systems that can be designed and operated to achieve their stated missions robustly. As is the case with other business systems, such as those designed to provide services and manufactured goods, there are benefits to managing variation such that the stakeholders within these business systems can focus more fully on the value added core processes that achieve the stated mission and less on activity responding to variations such as emergency procedures, regular medical interventions, delays, accelerations, backups, underutilized assets, unplanned overtime by staff and stock outs of material, equipment, people and space that are impacted in the course of delivering healthcare.

Currently, clinical process decisions have historically relied on the art of understanding symptoms and diagnosing causality much in alignment with the practice of the medical diagnosis arts. In an ever-evolving environment, judgment and experientially-developed mental models are utilized by the healthcare providers to utilize the information currently at hand to make decisions. Presented with similar data, the decision made from one caregiver to another typically exhibits a variation. Presented with partial information, which is the byproduct of being organized in functional departments, specialties, roles and by the nature of having partial and/or current or dated information availability on hand—clinical process decisions vary widely and typically are locally focused for lack of a systems view upstream and downstream of the decision point.

As a hospital processes care plans on an increasing patient load, these variations in medical condition and selected treatment plans disrupt the schedules of doctors, nurses and assets such as rooms and equipment. If there is protective capacity in these schedules and staff, the providers of care can manage variation while maintaining care quality. When randomness and interdependencies exceed the ability to serve, care providers are forced to make choices amongst poor alternative options; some one or some thing is going to be bottlenecked or overextended. Delays, queues, overtime, burnout and emotional decision making characterize systems that are overtaxed or beyond their ability to perform.

Typically, each procedure in a clinical information system, such as a radiology information system, is assigned a static duration (usually in minutes) set by a system administrator that determines the default estimate length of the procedure and the amount of time the procedure takes up on the scheduling grid. This information is used during the scheduling process to record procedure duration in the schedule. This approach to scheduling can create either under utilization of resources or risk patient safety and/or service satisfaction due to over utilization of resources at least in part in view of the variations and complications discussed above.

SUMMARY OF THE INVENTION

Certain embodiments provide systems and methods for self-updating procedure duration estimation for patient scheduling.

Certain embodiments provide a method for estimating procedure duration for scheduling in a clinical environment. The method includes establishing a default duration value for a procedure. The method also includes updating the default duration value based on historical procedure duration data. The method further includes providing a plurality of procedure durations including the updated default duration value to a user for selection. Additionally, the method includes scheduling a procedure using a user selected value for procedure duration.

Certain embodiments provide a scheduling system for scheduling procedures in a clinical environment. The scheduling system includes historical procedure data including stored duration values for a procedure. The scheduling system also includes a user interface providing scheduling and procedure duration information to a user for scheduling the procedure for a patient. The scheduling system further includes a scheduling engine estimating one or more duration values for the procedure for scheduling the procedure for a patient. The scheduling engine establishes a default duration value for a procedure and updating the default duration value based on the historical procedure duration data. The scheduling engine provides a plurality of procedure durations including the updated default duration value to the user for selection via the user interface. The scheduling engine schedules a procedure using a user selected value for procedure duration.

Certain embodiments provide a machine readable medium including a set of instructions for execution on a computing device. The set of instructions can include a duration routine establishing a default duration value for a procedure. The set of instructions can also include an update routine updating the default duration value based on historical procedure duration data. The set of instructions can further include an input routine providing a plurality of procedure durations including the updated default duration value to a user for selection. The set of instructions can also include a scheduling routine scheduling a procedure using a user selected value for procedure duration.

Figure 1:
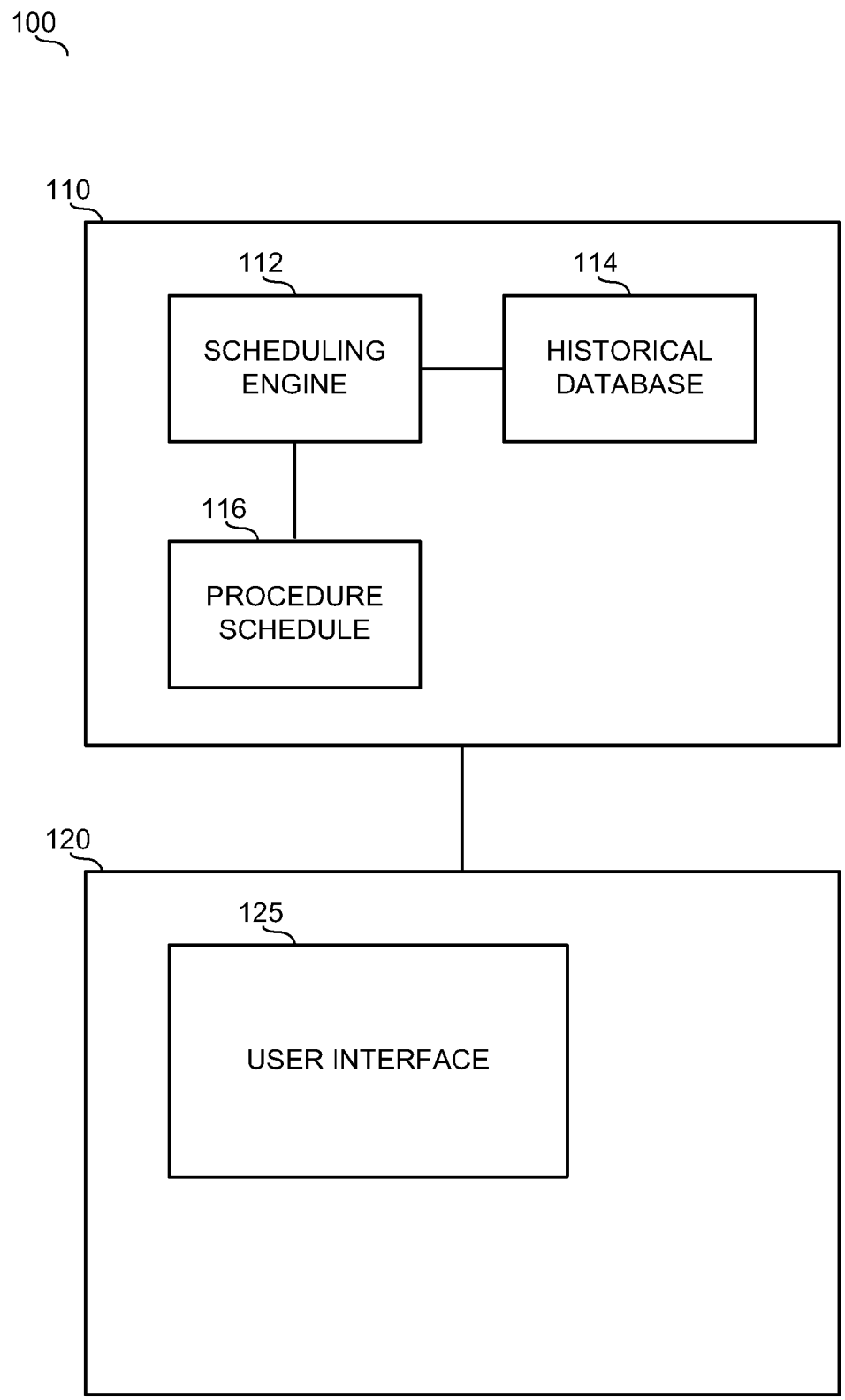
FIG. 1 depicts a block diagram of an example processing system for procedure duration estimation for patient scheduling in accordance with certain exemplary embodiments.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Certain example embodiments provide a self-updating mechanism that automatically analyzes historical data regarding actual durations of performed procedures to provide durations for scheduling of future procedures. Output of the mechanism can be used to update a default estimate duration for each procedure using an average duration based on historical data. The default procedure duration, as well as expected, pessimistic, and/or optimistic duration, can be provided to a user during the scheduling process to help allow the user to make better informed decision when entering patient appointments into a scheduling system.

Certain embodiments provide scheduling systems and methods that analyze actual duration for past procedures performed and use a weighting mechanism to assign more importance to the more recent duration instances. A statistical tool such as Exponentially Weighted Moving Average (EWMA) can be used for this. The relative weight of newer instances can be configurable by allowing a user and/or automated software program to adjust an alpha or scaling parameter in the EWMA equation.

For example, before attempting to schedule a procedure, the user is presented with the default procedure duration, as well expected, pessimistic and optimistic durations. Based on the additional information, the user can make scheduling decision. The user, such as a system administrator, can configure automatic use of the EWMA duration as the default duration. Alternatively, the use may choose to manually specify the default duration.

Procedure duration data can be tracked and/or entered manually by a user and/or automatically by a software program, for example. As duration data accumulates, future duration determination becomes more accurate. Patients can be made aware of procedure duration calculations as well as a scheduling user. Additionally, the user can return to a default or initial duration value for a procedure and/or manually adjust a scheduled duration value, for example. Procedure duration can be presented to a user and/or other viewer graphically, alphanumerically, etc., and can be shown for user re-entry, user point and click selection, etc.

Certain embodiments provide systems and methods to manage changes to a schedule to accommodate changes that are internally or externally induced in a way that reduces degradation of overall health delivery system throughput or quality. Certain embodiments provide systems and methods to review what has recently happened in a process, to view actual current process operations, and to view what is on the schedule looking forward into the near term future.

Certain embodiments are adaptable and dynamically configurable. Increased adaptability and dynamic configurability help clinical systems and personnel to function more reliably and to be robust to exogenous forces outside of process control such as what symptoms patients present with, time of emergency, volume of patient medical demand, and the like.

FIG. 1 depicts a block diagram of an example processing system 100 for procedure duration estimation for patient scheduling. As shown in FIG. 1, the processing system 100 includes a clinical information system 110 and a user workstation 120. The user workstation 120 includes a user interface 125 for display of and access to clinical information by a user. The clinical information system 110 includes a scheduling engine 112, a historical database 114, and a procedure schedule 116. The scheduling engine 112 can include a processor, such as any suitable processor, processing unit, or microprocessor, for example. Although not shown in FIG. 1, the scheduling engine 112 may be a multi-processor system and, thus, may include one or more additional processors that are communicatively coupled through a bus or other connection, for example. The processor includes and/or is in communication with a memory that includes instructions and data to, for example, generate the schedule 116 and provide the schedule 116 and other information to the user interface 125 for display to and interaction with a user via the workstation 120.

Components of the system 100 can be implemented in one or more components in hardware, software, and/or firmware, for example. Components of the system 100 that are implemented separately are in communication with each other via wired and/or wireless network, for example. For example, the workstation 120 communicates with the information system 110 via a wired or wireless data connection. The scheduling engine 112 and the database 114 can be included in a single information system 110 and/or may be divided among subsystems of the information system 110 in communication with each other, for example.

In certain embodiments, a moving average is used to estimate procedure duration for use in scheduling by the scheduling engine 112. A moving or rolling average refers to one of several techniques used to analyze time series data. For example, a simple moving average is an unweighted mean of a previous number of data points. A running average is an unweighted mean of all data collected up to a current point, for example. A weighted moving average is an average that includes multiplying factors to assign different weights to different data points, for example. In an embodiment, a weighted moving average includes weights that decrease arithmetically. An exponential moving average or an exponentially weighted moving average ("EWMA") applies weighting factors that decrease exponentially. The weighting for each older data point decreases exponentially, giving more importance to recent observations but not discounting older observations. A degree of weighting decrease can be expressed as a constant smoothing factor, which can be expressed in a variety of ways as a number between 0 and 1, a percentage, a number of N time period, etc. In certain embodiments, a higher smoothing factor discounts older observations at a faster rate. The scheduling engine 112 can use a moving average, such as an EWMA, to determine a procedure duration estimate based on available data. Such determination can be automatically used in scheduling and/or provided to a user via the user interface 125 on the workstation 120, for example.

In certain embodiments, the scheduling engine 112 automatically analyzes historical data related to actual procedure durations for performed procedures stored in the database 114. The output can be used to update a default estimated duration for each procedure with an average duration based on the historical data. The default procedure duration, as well the expected, pessimistic and optimistic durations, are then presented to a user during the scheduling process at the workstation 120 via the user interface 125. A user is then empowered to make an informed decision when entering patient appointment(s) into the schedule 116, for example. If no input is provided by the user, the scheduling engine 112 can default to a certain preselected type of value, such as the default estimate duration updated based on the average duration, the expected duration, the pessimistic duration, and/or the optimistic duration.

In certain embodiments, an initial duration value for each procedure can be set by software and/or a system administrator, for example. The scheduling engine 112 analyzes actual durations for past procedures performed and uses a weighting mechanism, such as an EWMA, to assign more importance to the more recent instances of the procedures. The relative weight of newer procedure duration instances can be configurable by allowing the system administrator to adjust the Alpha parameter or smoothing factor in the EWMA equation.

The scheduling engine 112 collects several statistics for each procedure including an expected duration (e.g., a best guess estimate based on historical data), a pessimistic duration (e.g., based on the lower 10th percentile of historical data), and an optimistic duration (e.g., based on the upper 90th percentile of historical data), for example. During the scheduling activity by the scheduling engine 112, before attempting to schedule the procedure, the user is presented with the default procedure duration, as well as the expected, pessimistic and optimistic durations. Based on the additional information, the user is able to make a more informed scheduling decision by selected one of the provided durations or a variant thereof. In certain embodiments, the scheduling engine 112 enables the system administrator to configure automatic use of the EWMA duration as the default duration. Alternatively, the system administrator may choose to manually specify the default duration, for example.

Thus, certain embodiments help to provide better informed scheduling for patient appointments. Higher efficiency in scheduling helps lead to higher productivity and better returns. Better resource utilization helps leads to better resource planning, more predictable working schedules, and higher job satisfaction for medical staff. Further, patient satisfaction can be improved by reducing wait time for appointments.

Presentation of multiple duration estimates (e.g., default procedure duration, expected procedure duration, pessimistic, procedure duration, and optimistic procedure duration) adds value to the scheduler when entering appointment for patients that is absent in prior systems. A weighted average can be determined based on actual data from recorded procedure history. This weighted average can be a self-updated, moving weighted average for procedure duration updating as new information is obtained. For example, an EWMA statistical model can be used indicate maximum, minimum, mean, median, etc., duration times for one or more same or similar procedures based on available duration data. Thus, actual procedure duration results can help determine the expected duration for future procedures. Procedure duration calculations can become more accurate as more data is gathered regarding similar procedures, for example.

Actual procedure duration data can be stored in a database or clinical information system, such as a radiology information system and/or clinical scheduling system. Actual start and finish and/or overall time data can be stored according to procedure and/or other criterion (e.g., physician, room, etc.).

In certain embodiments, procedure duration is provided based on an initial point or default value. This default value can be based on a preconfigured selection during installation and/or other user entry, for example. In certain embodiments, a user, such as a physician or technologist, can enter procedure start/end times, and a running process determines the actual duration for that procedure. For example, the procedure end is identified when an image is successfully captured. As another example, the procedure is deemed ended when a user manually clicks a start/stop button and/or otherwise selects an indicator. Time estimates for a procedure are generated based on the collected duration data and provided to a user for scheduling of future procedures. A user can switch back to the default value and/or another manually entered value if unsure of the provided estimates.

In certain embodiments, time estimates are provided according to a pessimistic/optimistic model—10% of the time procedure A will take X minutes; 20% of the time procedure A will take Y minutes; most of the time procedure A will take Z minutes, for example. The duration estimation information is provided to a user who is scheduling appointments (e.g., a receptionist, nurse, etc.) so that they can better make an informed decision and patient can be made aware of estimated procedure duration as well. In certain embodiments, a scheduling interface 125 appears as a calendar-based interface with available blocks of time for scheduling based on facility, room, physician, equipment, and/or other criterion, for example. Users are prompted to enter information to schedule a procedure. In certain embodiments, a user can manually enter a procedure duration in response to viewing duration values provides in alphanumeric and/or graphical form. In certain embodiments, a user can view procedure durations on a bell curve and select a desired time on a bell curve or other graphical representation, which will then automatically fill in the time in the schedule for the user, for example.

In certain embodiments, the scheduling engine 112 can include a plurality of modules for estimating procedure duration and scheduling procedures in a clinical calendar, for example. The scheduling engine 112 can include a duration estimation module configured to characterize average duration times and variations from average duration times for a given procedure or activity and a scheduling module configured to schedule procedures or activities in accordance with characterized times from the duration estimator module, for example. The user interface 125 can be configured to permit a user to visualize variation, to visualize scheduling opportunities and constraints, and to view information output for use in scheduling procedures and activities, for example.

The duration estimation module processes historical procedure duration data and measures variation so that procedure times are more accurate and so that schedule risk is reduced. The scheduling module reserves blocks of time for procedures in a clinical environment. In certain embodiments, the scheduling model can factor in preferences and availabilities as well as duration estimation to help achieve objectives such as case mix, outcomes, safety and to provide incentive for desired behaviors. The user interface 125 may include, for example, at least one of modules configured to permit a user to visualize variation, to visualize scheduling opportunities and constraints, and to provide output for use in scheduling procedures and activities, or combinations thereof.

The user interface 125 is configured to provide output for use in directing procedures and activities. The user interface 125 can be used to gather information that is later used to reduce variation and to interact with clinical process stakeholders in mediums that are natural extensions of their native environments. The user interface 125 may include computer display and/or reports, for example.

Clinical procedures have vast variation and yet advanced scheduling typically is made using a single prescribed duration time. When procedures take less than the forecast, valuable assets are underutilized and clinical flexibility is degraded because the availability is unanticipated/unactionable and further, downstream processes are impacted from patient handling, staffing and equipment turn around. When procedures take more time than forecasted, valuable assets are unavailable for other procedures that were scheduled thus backing up upstream processes, creating staffing shortfalls and fatigue stress from the emotional responses to schedule collapse and recovery.

Estimating the duration of a procedure has a number of difficulties. One forecast difficulty is the variation on single procedure cases that result from doctor/staff combinations, patient disease state severity, patient medical complications and physical attributes such as weight/height/body mass index (BMI)/surface area, information availability, equipment and supply availability, day of week, procedure prior and etc. Another still is wrong or non-recorded information such as, for example, time durations, and multiple procedures conducted with only a subset being recorded as actually having been conducted.

In certain embodiments, duration estimation is accomplished depending upon the information initially available, for example a history of procedures, and then a learning or feedback loop is implemented that reduces the forecast error by incorporating additional information such as accurate case times and well measured descriptive attributes that serve as leading indicators, for example. In the absence of a historical record, duration estimation can be achieved via expert input. Experts include consensus of relevant professionals collated via industry working groups, societies and academic study, nursing, administrators, anesthesiologists and surgeons, for example. Historical data of recorded procedures and their duration are more desirous than strictly expert opinion. A preliminary analytical step can be to characterize the accuracy (mean and statistical variation) of historical procedure duration vs. actual duration for like cases.

Earlier than anticipated procedure finishes may afford additional schedule margin if only visibility existed either at the time of booking or once the procedure(s) began that a room would have capacity. Likewise, delays ascertainable at scheduling or during the procedure, if better understood, can impact the interdependencies downstream of the procedure both for that clustering of patient/staff/asset and for other impacted clusters. Schedule robustness can be attained from planning the median, average and a notion of anticipated variation such as standard deviation. A history of procedures can be combined into a relational database or spreadsheet or analytical platform capable of data mining with data incorporated into a data repository, for example.

The scheduling engine 112 can utilize duration information and input from the user to schedule room, staff, equipment, and patients according to available blocks of time and space. Healthcare blocks are allocated based upon past, evolutionary activity. Staff, rooms, procedures, patient demographics, clinical specialties and competitors all drive changing assumptions of former time and space allocations. Thus, methods and systems described herein may enable increased throughput, schedule risk reduction, incentive driven policy, preferences and a consistent environment. Hospitals, surgeons, patients and staff can be beneficiaries.

In operation, the user interface 125 and/or other input can provide input data such as utilization by surgeons, groups eligible for block time and time, room and staff preferences, for example. As used herein, the term "block" refers to an allotted time frame such as for scheduling an operating room or clinical procedure room, e.g. an imaging room in a hospital. Historical block allocation data can be characterized by data mining to describe utilization by surgeon, for example. Hospital administration can determine groups eligible for block time and preliminarily reconcile requests. Duration estimates are determined based on historical data and provided to a user (and/or automatically applied). Scheduling and resource/personnel assignments can then be made. Having the ability to communicate visually helps with rapid understanding. In certain embodiments, a 'cockpit' describing the historical fact patterns and current operating results helps to facilitate conversation.

In certain embodiments of the present invention, the user interface 125 is provided in order to convey information to a user for use in scheduling procedures. In an exemplary embodiment, the user interface 125 provides an ability to monitor activities for a given day.

By having a procedure finish before the schedule, potential scheduling flexibility is lost for other issues that inevitably arise during the day such as staff availability, rooms and equipment constraints. Potential throughput capacity might also be impacted in that over the course of a day, one or more additional procedures could be inserted into the schedule.

Figure 2:
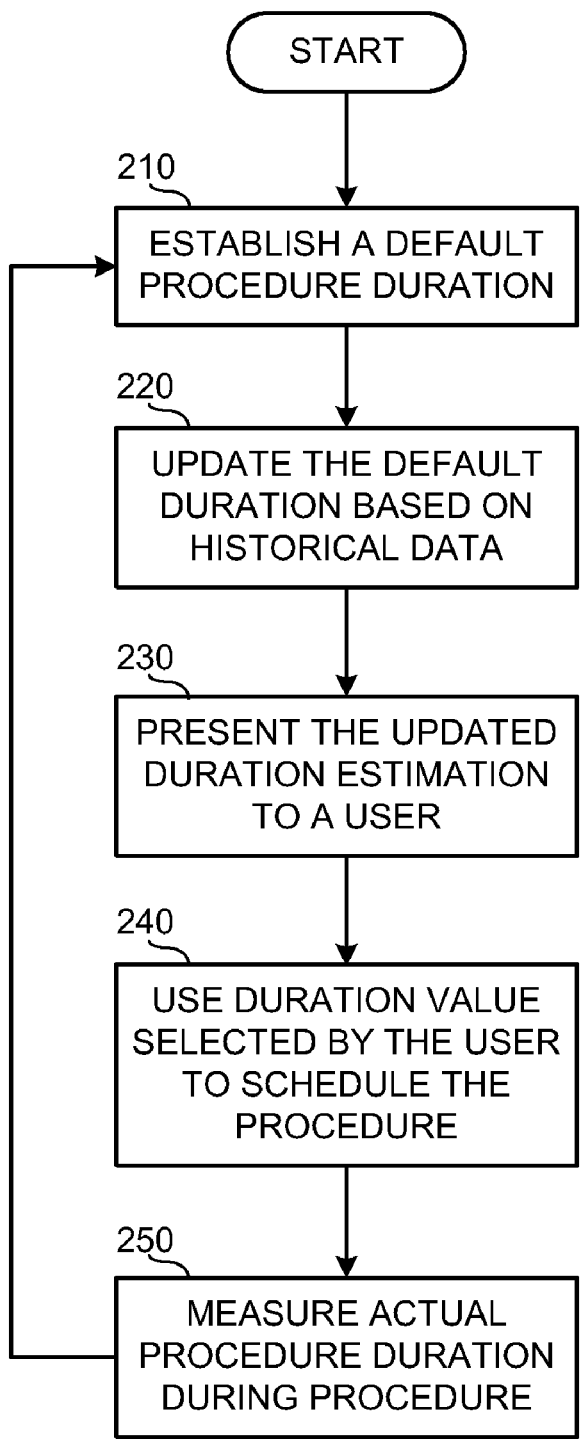
FIG. 2 illustrates a flow diagram for a method for procedure duration estimation and scheduling in accordance with certain exemplary embodiments.

FIG. 2 illustrates a flow diagram for a method 200 for procedure duration estimation and scheduling. At 210, a default duration is established. For example, a system administrator, clinician, database, software program, etc. can specify a default duration for each of one or more procedures.

At step 220, the default procedure duration is updated based on available historical data. For example, an EWMA algorithm can be applied using the default procedure duration and historical duration data related to the procedure recorded and stored from prior procedures.

At step 230, the updated procedure duration estimation is presented to a user. In certain embodiments, a plurality of duration estimations can be presented to the user. For example, the default procedure duration can be presented to the user in conjunction with an expected procedure duration, a pessimistic procedure duration, and an optimistic procedure duration based on historical duration data.

At step 240, a duration value is selected by the user and used to schedule the procedure. For example, the user can select one of the default procedure duration, the expected procedure duration, the pessimistic procedure duration, and the optimistic procedure duration and use that time value to block or reserve time and resource in a clinical schedule for the procedure.

At step 250, the procedure is performed and actual duration is measured. For example, a user can manually track and enter procedure time, which is then added to the historical data used to estimate future procedure duration estimations. As another example, computer software and/or hardware can be used to automatically track actual procedure duration based on input and/or output to the software and/or hardware during the procedure.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 3:
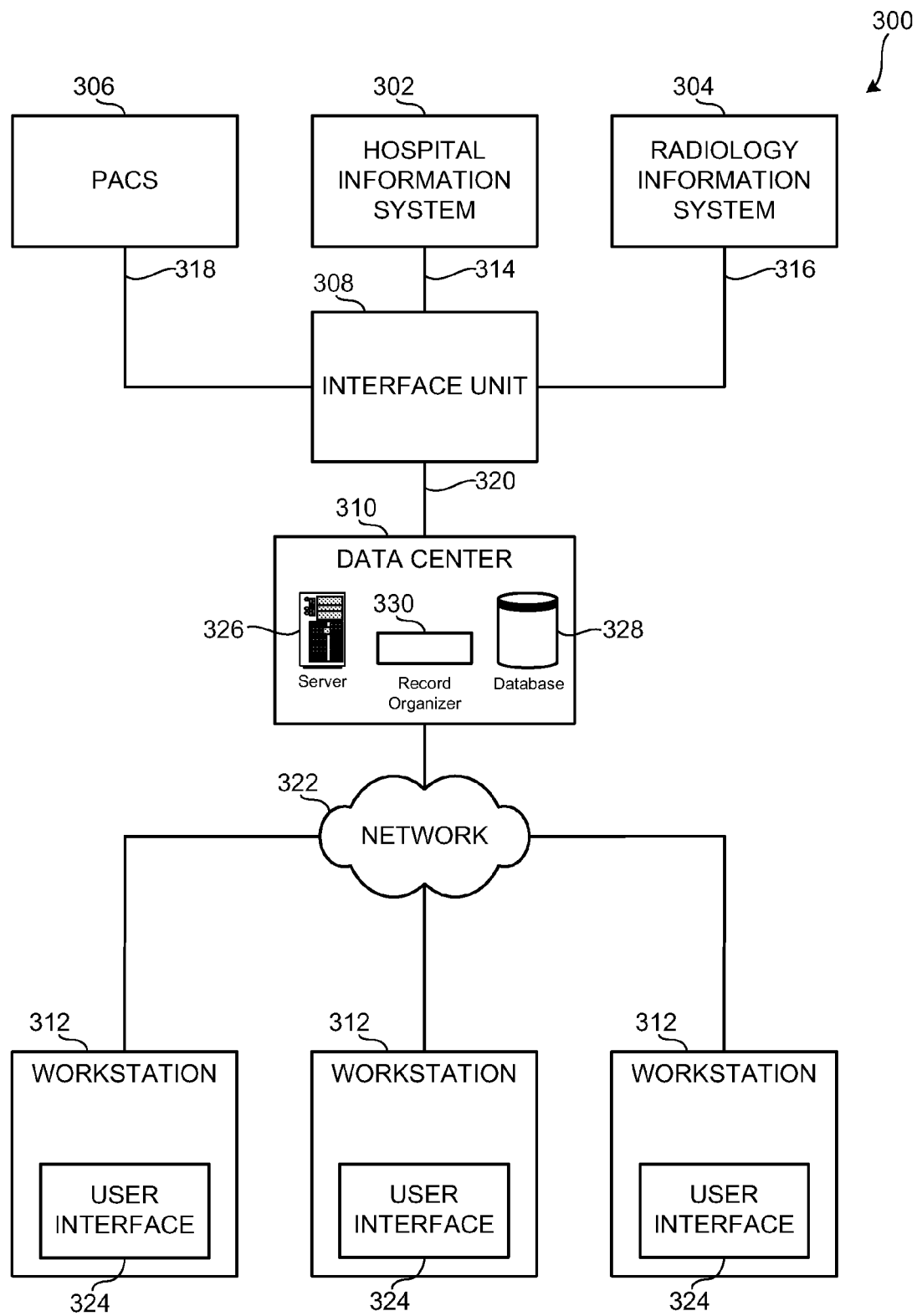
FIG. 3 shows a block diagram of an example clinical information system capable of implementing the example methods and systems described herein to provide clinical procedure duration estimation and scheduling.

FIG. 3 shows a block diagram of an example clinical information system 300 capable of implementing the example methods and systems described herein to provide clinical procedure duration estimation and scheduling. The example clinical information system 300 includes a hospital information system ("HIS") 302, a radiology information system ("RIS") 304, a picture archiving and communication system ("PACS") 306, an interface unit 308, a data center 310, and a plurality of workstations 312. In the illustrated example, the HIS 302, the RIS 304, and the PACS 306 are housed in a healthcare facility and locally archived. However, in other implementations, the HIS 302, the RIS 304, and/or the PACS 306 may be housed one or more other suitable locations. Furthermore, one or more components of the clinical information system 300 may be combined and/or implemented together. For example, the RIS 304 and/or the PACS 306 may be integrated with the HIS 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the HIS 302, the RIS 304, and/or the PACS 306. Preferably, information (e.g., scheduling, test results, observations, diagnosis, etc.) is entered into the HIS 302, the RIS 304, and/or the PACS 306 by healthcare practitioners (e.g., radiologists, physicians, and/or technicians) before and/or after patient examination.

The HIS 302 stores medical information such as clinical reports, patient information, and/or administrative information received from, for example, personnel at a hospital, clinic, and/or a physician's office. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the HL-7 (Health Level Seven) clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the HIS 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider (ASP) and is located in a centralized location that may be accessed by a plurality of systems and facilities (e.g., hospitals, clinics, doctor's offices, other medical offices, and/or terminals). In some examples, the data center 310 may be spatially distant from the HIS 302, the RIS 304, and/or the PACS 306 (e.g., at General Electric® headquarters).

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
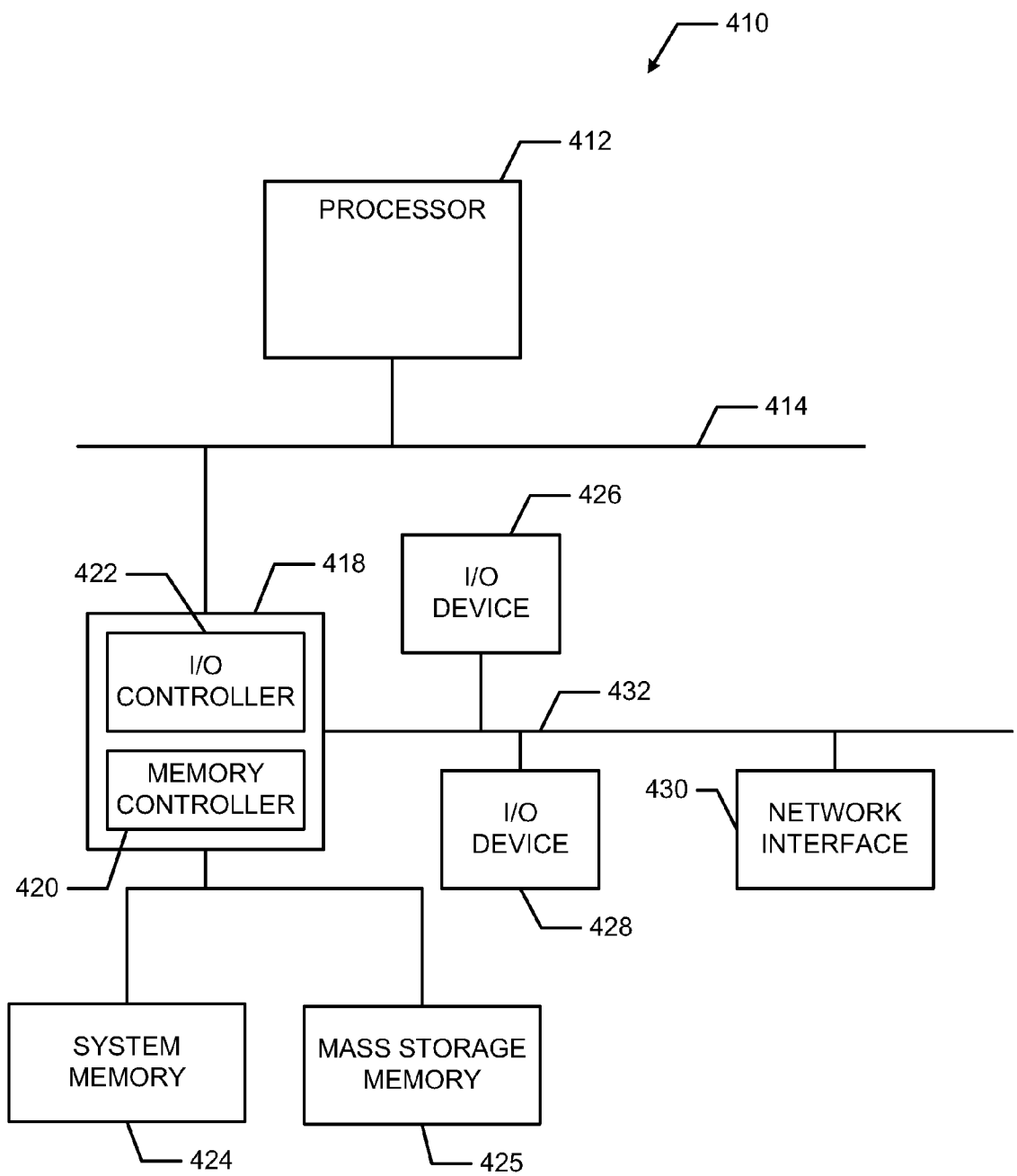
FIG. 4 is a block diagram of an example processor system that may be used to implement systems and methods described herein.

FIG. 4 is a block diagram of an example processor system 410 that may be used to implement systems and methods described herein. As shown in FIG. 4, the processor system 410 includes a processor 412 that is coupled to an interconnection bus 414. The processor 412 may be any suitable processor, processing unit, or microprocessor, for example. Although not shown in FIG. 4, the system 410 may be a multi-processor system and, thus, may include one or more additional processors that are identical or similar to the processor 412 and that are communicatively coupled to the interconnection bus 414.

The processor 412 of FIG. 4 is coupled to a chipset 418, which includes a memory controller 420 and an input/output ("I/O") controller 422. As is well known, a chipset typically provides I/O and memory management functions as well as a plurality of general purpose and/or special purpose registers, timers, etc. that are accessible or used by one or more processors coupled to the chipset 418. The memory controller 420 performs functions that enable the processor 412 (or processors if there are multiple processors) to access a system memory 424 and a mass storage memory 425.

The system memory 424 may include any desired type of volatile and/or non-volatile memory such as, for example, static random access memory (SRAM), dynamic random access memory (DRAM), flash memory, read-only memory (ROM), etc. The mass storage memory 425 may include any desired type of mass storage device including hard disk drives, optical drives, tape storage devices, etc.

The I/O controller 422 performs functions that enable the processor 412 to communicate with peripheral input/output (I/O) devices 426 and 428 and a network interface 430 via an I/O bus 432. The I/O devices 426 and 428 may be any desired type of I/O device such as, for example, a keyboard, a video display or monitor, a mouse, etc. The network interface 430 may be, for example, an Ethernet device, an asynchronous transfer mode ("ATM") device, an 802.11 device, a DSL modem, a cable modem, a cellular modem, etc. that enables the processor system 410 to communicate with another processor system.

While the memory controller 420 and the I/O controller 422 are depicted in FIG. 4 as separate blocks within the chipset 418, the functions performed by these blocks may be integrated within a single semiconductor circuit or may be implemented using two or more separate integrated circuits.

Thus, certain embodiments provide systems and methods to provide decision support as to where best, given one or more process objectives and duration estimates, to add and insert task(s). Certain embodiments provide systems and methods to dynamically and adaptively determine procedure durations based on accumulating and updating historical information from actual procedure durations. Certain embodiments provide a variety of duration options for user selection to facilitate scheduling.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represents examples of corresponding acts for implementing the functions described in such steps.

For example, certain embodiments can include a machine readable medium including a set of instructions for execution on a computing device. The set of instructions can include a duration routine establishing a default duration value for a procedure. The set of instructions can also include an update routine updating the default duration value based on historical procedure duration data. The set of instructions can further include an input routine providing a plurality of procedure durations including the updated default duration value to a user for selection. The set of instructions can also include a scheduling routine scheduling a procedure using a user selected value for procedure duration.

In certain embodiments, the machine readable medium can include a feedback routine measuring an actual duration for the procedure and providing feedback regarding the actual duration to the historical procedure duration data used to update the default duration value.

In certain embodiments, the update routine updates the default duration value by applying a weighted moving average to the default duration value using the historical procedure duration data. The weighted moving average may be an exponentially weighted moving average, for example. The exponentially weighted moving average includes a scaling parameter, the scaling parameter adjustable to configurably weight newer duration values compared to older duration values.

In certain embodiments, the plurality of procedure durations includes an expected procedure duration value, an optimistic procedure duration value, and a pessimistic procedure duration value, for example.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any clinical software feedback and dynamic scheduling/planning system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A computer-implemented method for estimating clinical procedure duration for scheduling in a clinical environment, said method comprising:
   establishing a default duration value for a clinical procedure;
   automatically updating, using a processor, the default duration value based on an automated analysis of stored historical procedure duration data related to the procedure, the updating comprising applying a weighted moving average to the default duration value using the historical procedure duration data, the weighted moving average comprising an exponentially weighted moving average including a scaling parameter, the scaling parameter adjustable to configurably weight newer duration values compared to older duration values;
   providing, using a processor, a plurality of procedure durations including the updated default duration value to a user for selection with respect to the clinical procedure;
   scheduling, using a processor, the clinical procedure using a user selected value for procedure duration;
   dynamically measuring, using a processor, an actual duration for the clinical procedure based on automated software measurement; and
   providing feedback regarding the actual duration to the historical procedure duration data used to adaptively update the default duration value.

2. The method of claim 1, wherein the providing a plurality of procedure durations including the updated default duration value further comprises providing the user with a plurality of duration values for selection, the plurality of duration values including an expected procedure duration value, an optimistic procedure duration value, and a pessimistic procedure duration value.

3. The method of claim 1, wherein the providing a plurality of procedure durations including the updated default duration value to a user for selection further comprises providing a graphical representation of the plurality of procedure durations to the user and allowing the user to select a procedure duration value from the graphical representation.

4. A scheduling system for scheduling procedures in a clinical environment, said scheduling system comprising:
   a processor coupled to a memory,
   wherein the memory includes historical procedure data including stored duration values for a procedure and wherein the processor is programmed to implement:
   a user interface providing scheduling and procedure duration information to a user for scheduling the procedure for a patient; and
   a scheduling engine estimating one or more duration values for the procedure for scheduling the procedure for a patient, the scheduling engine establishing a default duration value for a procedure and automatically updating the default duration value based on the historical procedure duration data, wherein the scheduling engine dynamically measures an actual duration for the procedure based on automated software measurement and provides feedback regarding the actual duration to the historical procedure data used to adaptively update the default duration value, the scheduling engine providing a plurality of procedure durations including the updated default duration value to the user for selection via the user interface, the scheduling engine scheduling a procedure using a user selected value for procedure duration,
   wherein the scheduling engine applies an exponentially weighted moving average to the default duration value to update the default duration value using the historical procedure duration data, the exponentially weighted moving average includes a scaling parameter, the scaling parameter adjustable to configurably weight newer duration values compared to older duration values.

5. The system of claim 4, wherein the plurality of procedure durations includes an expected procedure duration value, an optimistic procedure duration value, and a pessimistic procedure duration value.

6. The system of claim 4, wherein the plurality of procedure durations are provided via the user interface by a graphical representation of the plurality of procedure durations to the user, the user interface allowing the user to select a procedure duration value from the graphical representation.

7. A tangible machine readable storage medium including a set of instructions for execution on a computing device, the set of instructions comprising:

a duration routine establishing a default duration value for a procedure;

an update routine updating the default duration value based on an automated analysis of historical procedure duration data related to the procedure, the update routine updating the default duration value by applying an exponentially weighted moving average to the default duration value using the historical procedure duration data, the exponentially weighted moving average including a scaling parameter, the scaling parameter adjustable to configurably weight newer duration values compared to older duration values;

an input routine providing a plurality of procedure durations including the updated default duration value to a user for selection;

a scheduling routine scheduling a procedure using a user selected value for procedure duration;

a feedback routine dynamically measuring an actual duration for the procedure and automatically providing feedback regarding the actual duration to the historical procedure duration data used to adaptively update the default duration value.

8. The machine readable medium of claim 7, wherein the plurality of procedure durations includes an expected procedure duration value, an optimistic procedure duration value, and a pessimistic procedure duration value.

* * * * *